US007410644B2

(12) United States Patent
Schlom et al.

(10) Patent No.: US 7,410,644 B2
(45) Date of Patent: Aug. 12, 2008

(54) RECOMBINANT POX VIRUS FOR IMMUNIZATION AGAINST TUMOR-ASSOCIATED ANTIGENS

(75) Inventors: Jeffrey Schlom, Potomac, MD (US); Dennis L. Panicali, Acton, MA (US); Linda R. Gritz, Somerville, MA (US); Gail P. Mazzara, Winchester, MA (US)

(73) Assignee: The United States of America as represented by the Department of Health and Human Services, Rockville, MD (US)

( * ) Notice: Subject to any disclaimer, the term of this patent is extended or adjusted under 35 U.S.C. 154(b) by 991 days.

(21) Appl. No.: 10/197,127

(22) Filed: Jul. 17, 2002

(65) Prior Publication Data
US 2003/0003079 A1 Jan. 2, 2003

Related U.S. Application Data (63) Continuation of application No. 08/686,280, filed on Jul. 25, 1996, now abandoned.

(51) Int. Cl.
*A61K 39/275* (2006.01)
*A61K 39/12* (2006.01)
(52) U.S. Cl. .................... 424/232.1; 514/44; 424/199.1; 424/93.2; 424/93.6
(58) Field of Classification Search .................... 514/2; 435/320.1
See application file for complete search history.

(56) References Cited

U.S. PATENT DOCUMENTS

| 5,174,993 | A | 12/1992 | Paoletti |
| 5,266,313 | A | 11/1993 | Esposito et al. |
| 5,382,425 | A | 1/1995 | Cochran et al. |

FOREIGN PATENT DOCUMENTS

| WO | WO 92/19266 A1 | | 11/1992 |
| WO | WO 94/16176 A1 | | 8/1994 |
| WO | WO 96/10419 A2 | | 4/1996 |
| WO | WO 96/10419 A3 | | 4/1996 |
| WO | WO 96/11279 | * | 4/1996 |
| WO | WO 96/11279 A2 | | 4/1996 |
| WO | WO 96/11279 A3 | | 4/1996 |
| WO | WO 96/26271 A1 | | 8/1996 |
| WO | WO 97/03203 A3 | | 1/1997 |

OTHER PUBLICATIONS

Kundig et al (Vaccine, 1993, 11:1154-1158).*
ICTVbB Index of Viruses, pp.1-10.*
"The Assessment of Future Scientific Needs for Live Variola Virus" p. 1-3; Chapter II, p. 1-6.*
"Third World Network Biosafety information service", May 19, 2005, p. 1-3.*
Von Mehren et al (Clinical Cancer Research, 2000, 6:2219-2228).*
Hodge et al (Vaccine, 1997, 15:759-768).*
Hodge et al II (Cancer Research, 1995, 15:3598-603).*
Ontario Ministry of Agriculture Food and Rural Affairs "fact sheet" p. 1-12.*
Marshall et al (J Clinical Oncology, 2000, 18:3964-3973).*
Cooney et al (The Lancet, 1991, 337:567-572).*
Kass-Eisler et al (Gene Therapy, Feb. 1996, 3:154-162).*
Hellstrom, K.E., et al., Adv. Cancer Res. 12:167-223 (1969).
Greenberg, P.D., Advances in Immunology, 49: 281-355 (1991).
Boon, T., et al., Annu. Rev. Immunol. 12:337-365 (1994).
Brithcard, V., et al., J. Exp. Med. 178:489-495 (1993).
Cox, A.L., et al., Science 264:716-719 (1994).
Houghton, A.N., J. Exp. Med. 180:1-4 (1994).
Pardoll, D.M., Nature 369:357-358 (1994).
Kawakami, Y., et al., Proc. Natl. Acad. Sci. U.S.A. 91:3515-3519 (1994).
Kawakami, Y., et al., Proc. Natl. Acad. Sci. U.S.A. 91:6458-6462 (1994).
Muraro, R., et al., Cancer Res. 4S:5769-5780 (1985).
Kantor, J., et al., J. Natl. Cancer Inst. 84:1084-1091 (1992).
Robbins, P.F., et al., Cancer Res. 51:3657-3662 (1991).
Kantor, J., et al., Cancer Res. 52:6917-6925 (1992).
Wang, M.C., et al., Meth. Cancer Res. 19:179-197 (1982).
Carter, H.B., et al., Cancer Research 52:3323-3328 (1992).
Austin, F.C., et al., Adv. Cancer Res. 50:301-345 (1979).
Taylor, J., et al., Vaccine 6:497-503 (1988).
Technological Advances in Vaccine Development (Alan R. Liss, Inc.) pp. 321-334.
Wild, T.F., et al., Vaccine 8:441-442 (1990).
Balloul, et al., Cell Mol. Biol. 40 (Suppl. I.):49-59 (1994).
Irvine, et al., Vaccine Research, 2(2):79-94 (1993).
Hodge, et al., Int. J. Cancer 63:231-237 (1995).
Taang et al., J. Nat'l Cancer Inst., 87(13):982-990 (1995).
Bu et al., J. of Immunotherapy 14:127-135 (1993).
Acres et al., Int. J. Cancer 63:31-237 (1995).
Tartaglia et al., *J Virol* 67 (1993) 2370-2375.
Paoletti. 1996., *PNAS* 93:11349-11353.
Romero et al., *Vaccine* 11(1993) 737-742.
Therasse P. Arbuck SG, Eisenhauer EA, Wanders J, Kaplan RS, Rubinstein L. et al. New guidelines to evaluate the response to treatment in solid tumors. European Organization for Research and Treatment of Cancer, National Cancer Institute of the United States, National Cancer Institute of Canada. J Natl Cancer Inst 2000;92:205-16.
Therasse P, Eisenhauer EA, Verweij J. RECIST revisited: a review of validation studies on tumor assessment. Eur J Cancer 2006;42:1031-9.
Tuma RS. Sometimes size doesn't matter: reevaluating RECIST and tumor response rate endpoints, J Natl Cancer Inst. 2006;98(18):1272-4.

(Continued)

*Primary Examiner*—Larry Helms
*Assistant Examiner*—Laura B Goddard
(74) *Attorney, Agent, or Firm*—Leydig, Voit & Mayer, Ltd.

(57) ABSTRACT

Recombinant pox viruses capable of expressing cell-encoded, tumor-associated antigens are disclosed. The recombinant viruses are useful for evoking an immune response against the antigen.

9 Claims, 7 Drawing Sheets

OTHER PUBLICATIONS

Gore ME, Escudier B. Emerging efficacy endpoints for targeted therapies in advanced renal cell carcinoma. Oncology (Williston Park). 2006;20(6 Suppl 5):19-24. Review.

Hoos A, Parmiani G, Hege K, Sznol M, Loibner H, Eggermont A, et al. A clinical development paradigm for cancer vaccines and related biologics, J Immunother 2007;30:1-15. Review.

Escudier B, Eisen T, Sadler WM, Szczylik C, Oudard S, Siebels M, et al. Sorafenib in advanced clear-cell renal-cell carcinoma. N Engl J Med 2007;356:125-34.

Hodge JW, Scholm J, Abrams SI, Vaccines and immunostimulants. In: Kufe DW, Bast Jr. RC, Hait WN, Hong WK, Pollack RE, Weichselbaum RR, et al., eds. Holland-Frei Cancer Medicine 7, 7th ed. Hamilton, Ontario: BC Decker; 2006:786-801.

Arlen PM, Gulley JL, Parker C, Skarupa L, Pazdur M, Panicali D, et al. A randomized phase II study of concurrent docetaxel plus vaccine versus vaccine alone in metastatic androgen independent prostate cancer. Clin Cancer Res 2006;12:1260-9. http://clincancerres.aacrjournals.org/cgi/content/full/12/4/1260.

Arlen PM, Gulley JL, Todd N, Lieberman R, Steinberg SM, Morin S, Bastian A, Marte J, Tsand K-Y, Beetham P, Grosenbach DW, Scholm J, Dahunt W. Antiandrogen, vaccine and combination therapy in nonmetastatic hormone refractory prostate cancer patients. J. Urol. 174:539-546,2005. http:/linkinghub.elsevier.com/retrieve/pii/S0022534701683034.

Madan RA, Gulley JL, Dahut WL, Steinberg S, Liewehr D, Scholm J, et al. An analysis of the 5-year overall survival (OS) in non-metastatic androgen independent prostate cancer (AIPC) patients (pts) treated with nilutamide (N), vaccine (V), and combination therapy. 2007 Prostate Cancer Symposium. Abstract (in press).

Akagi, J, Hodge J, McLaughlin JP, Gritz L, Mazzara G, Kufe D, Scholm J, Kantor JA. et al. Therapeutic antitumor response after immunization with an admixture of recombinant vaccinia viruses expressing a modified MUC1 gene and the murine T-cell costimulatory molecule B7. Journal of Immunotherapy 20(1);38-47, 1997.

\* cited by examiner

RECOMBINANT POX VIRUS FOR IMMUNIZATION AGAINST TUMOR-ASSOCIATED ANTIGENS

CROSS-REFERENCE TO RELATED APPLICATIONS

This application is a Continuation of U.S. Ser. No. 08/686,280 filed on Jul 25, 1996, now abandoned.

BACKGROUND OF THE INVENTION

The immunotherapeutic approach to the treatment of cancer is based on the observation that human tumor cells express a variety of tumor-associated antigens (TAAs) that are not expressed in normal tissues. These antigens, which include viral tumor antigens, cellular oncogene proteins, and tumor-associated differentiation antigens, can serve as targets for the host immune system and elicit responses which result in tumor destruction. This immune response is mediated primarily by lymphocytes; T cells in general and class I MHC-restricted cytotoxic T lymphocytes in particular play a central role in tumor rejection. Hellstrom, K. E., et al., (1969) Adv. Cancer Res. 12:167-223; Greenberg, P. D. (1991) in *Advances in Immunology*, vol. 49 (Dixon, D. J., ed.), pp 281-355, Academic Press, Inc., Orlando, Fla. Unfortunately, as evidenced by the high incidence of cancer in the population, the immune response to neoplastic cells often fails to eliminate tumors. The goal of active cancer immunotherapy is the augmentation of anti-tumor responses, particularly T cell responses, in order to effect complete tumor destruction.

Most attempts at active immunization against cancer antigens have involved whole tumor cells or tumor cell fragments. However, the cloning of TAAs recognized by CD8+ T cells has opened new possibilities for the immunotherapy of cancer based on the use of recombinant or synthetic anti-cancer vaccines. Boon, T., et al.,(1994) Annu. Rev. Immunol. 12:337-365; Brithcard, V., et al., (1993) J. Exp. med. 178:489-495; Cox, A. L., et al., (1994) Science 264:716-719; Houghton, A. N. (1994) J. Exp. Med. 180:1-4; Pardoll, D. M. (1994) Nature 369:357-358; Kawakami, Y., et al., (1994) Proc. Natl. Acad. Sci. U.S.A. 91:3515-3519; Kawakami, Y., et al., (1994) Proc. Natl. Acad. Sci. U.S.A. 91:6458-6462.

Two such antigens have been designated MART-1 (Melanoma Antigen Recognized by T cells-1) and gp100. *Proc. Natl. Acad. Sci. U.S.A.* 91:3515-3519. MART-1 and gp 100 appear to be expressed in virtually all fresh and cultured melanomas. With the exception of melanocyte and retina, no normal tissues express the antigens. The antigens may be responsible for mediating tumor regression in patients with advanced melanoma, since the tumor-infiltrating lymphocytes (TIL) used to identify MART-1 and gp100 were capable of effecting tumor regression in vivo. Thus, immunization of melanoma patients with MART-1 or gp100 may boost their cellular immune responses against their cancers.

The use of recombinant vaccinia viruses for anti-tumor immunotherapy has been reviewed. (Hu, S. L., Hellstrom, I., and Hellstrom K. E. (1992) in Vaccines: New Approaches to Immunological Problems (R. W. Ellis, ed) pp 327-343, Butterworth-Heinemann, Boston.) Anti-tumor responses have been elicited using a recombinant vaccinia virus expressing a TAA designated carcinoembryonic antigen (CEA). CEA is a glycoprotein expressed at high level on the surface of nearly all tumors of the gastrointestinal tract, as well as on many mammary carcinomas and lung adenocarcinomas. (Muraro, R., et al., (1985) *Cancer Res.* 4S:5769-5780.) A recombinant vaccinia virus that expresses CEA (Kantor, J., et al. (1992) *J. Natl. Cancer Inst.* 84:1084-1091) was evaluated using a murine tumor model in which the human CEA gene was transduced into murine colon carcinoma cells. (Robbins, P. F., et al. (1991) *Cancer Res.* 51:3657-3662.) Mice immunized with the CEA/vaccinia recombinant were resistant to the growth of subsequently transplanted CEA-expressing tumors. Moreover, when mice bearing established CEA-transduced murine carcinomas were treated with the recombinant virus, the tumors showed greatly reduced growth or complete regression. In rhesus monkeys, which carry an antigen on the surface of their granulocytes that cross-reacts with human CEA, immunization with the recombinant elicited anti-CEA antibodies, delayed type hypersensitivity, and lymphoproliferative responses. (Kantor, J., et al. (1992) *Cancer Res.* 52:6917-6925.) No toxicity was observed.

Prostate-specific antigen (PSA) is a 33,000-34,000 dalton glycoprotein that is produced in normal, benign, and cancerous prostate epithelia, but not in other normal or malignant tissues. (Wang, M. C., et al. (1982) *Meth Cancer Res.* 19): 179-197.) PSA is secreted into prostatic fluid and seminal plasma. (See, Wang, et al.) Elevation of PSA levels in serum is correlated with growth of the prostate, and prostate cancer patients show an exponential increase in PSA levels. (Carter, H. B., et al. (1992) *Cancer Research* 52:3323-3328.) Due to its tissue specificity, PSA is a potential target antigen for immunotherapy against prostate cancer.

A number of laboratories have explored the use of recombinant poxviruses that express specific TAAs as immunotherapeutic vaccines. The ability of recombinant poxviruses expressing a variety of antigens to serve as potential vaccines for the prevention of infectious disease has been well-documented. Immunization with live recombinant pox virus allows expression of foreign antigens that are presented to the immune system together with highly immunogenic, virus proteins, which may act as adjuvants to enhance immune responses to the foreign antigen. Austin, F. C., et al. (1979) *Adv. Cancer Res.* 50:301-345. Finally, poxviruses are not oncogenic and do not integrate into the host cell genome, as replication and transcription of genetic material occurs in the cytoplasm of the infected cell.

Viruses of the family Poxviridae (pox viruses) are useful as vectors for the delivery of foreign genes and gene products in many clinical and research settings. Pox viruses of the genus Orthopoxvirus, particularly vaccinia, are used for several reasons. Among these are: (a) its wide use in humans in the eradication of smallpox; (b) its ability to infect a wide range of cells, including professional antigen presenting cells, and express the inserted gene product (i.e. foreign gene product) in a manner that has the potential to be processed in the context of class I and/or class II MHC molecules; and (c) use as a recombinant vaccine in the treatment of certain tumors (Kantor, J. et al. (1992)).

Fowlpox virus (FPV) is a member of the avipox virus family. Productive FPV infection is restricted in vivo to cells derived from avian species; however, FPV-mediated gene expression does occur in infected non-avian cells. Taylor, J. et al., (1988) Vaccine 6:497-503. Fowlpox virus based recombinant vaccines are described in: *Technological Advances in Vaccine Development* (Alan R. Liss, Inc.) pp. 321-334. Furthermore, in vivo FPV-mediated gene expression in several mammalian species has been demonstrated. Six non-avian species immunized with live recombinant fowlpox virus expressing the rabies glycoprotein developed antibodies against this glycoprotein. Immunization with this recombinant FPV elicited antibodies against this glycoprotein. Immunization with this recombinant FPV partially protected mice, cats, and dogs against a rabies virus challenge. There was no manifestation of proliferative infection or overt disease in any animals immunized with a variety of doses of live recombinant FPV.

Taylor, J., et al., (1988) Vaccine 6:497-503. In another study, a recombinant FPV containing a measles fusion protein was shown to partially protect mice against lethal challenge the measles virus, although antibodies against the fusion protein were not detected. Wild, T. F., et al., (1990) Vaccine 8:441-442. It was therefore postulated that protection was mediated by cellular immune responses. These results suggest that recombinant FPV may have utility as a safe and effective alternative to vaccinia virus as a vaccine vector.

SUMMARY OF THE INVENTION

The present invention relates to recombinant pox viruses capable of expressing cell-encoded tumor associated antigens and/or immunomodulators.

Recombinant pox virus capable of expressing a cell-encoded tumor-associated antigen are produced by integrating into the pox virus genome sequences encoding the antigen or immunogenic portions thereof. Tumor associated antigens include molecules expressed by tumor cells (e.g. carcinoembryonic antigen, prostate-specific antigen (PSA), MUCIN (MUC-1), melanoma associated antigens such as MART-1, etc.). Immunomodulators include interleukin 2, B7.1 and B7.2.

Particularly preferred recombinant pox viruses include TBC-CEA (vaccinia, CEA), PROSTVAC (vaccinia, PSA), rV-B7.1 (vaccinia, B7), rF-B7.1 (fowlpox, 7.1), rF-CEA (fowlpox, CEA), rV-MUC-1 (vaccinia, MUC-1) and rF-PSA (fowlpox, PSA).

DETAILED DESCRIPTION OF THE INVENTION

Pox viruses serve as effective vectors for inducing immunity against tumor-associated antigens.

Particularly preferred tumor-associated antigens are cell surface molecules. These are positioned for recognition by elements of the immune systems and thus are excellent targets for immunotherapy.

Tumor-associated antigens are expressed by certain tumor cells and provide effective targets for immunotherapy. Some examples are carcinoembryonic antigen (CEA) and prostate-specific antigen (PSA).

Immunomodulators can regulate immune responses, increasing the likelihood of a sufficient cellular immune response occurring, (e.g. IL-2) or can provide cellular ligand necessary for stimulating a CTL response (e.g. B7.1 or B7.2)

Basic techniques for preparing pox viruses containing a heterologous DNA sequence encoding the tumor-associated antigen known to the skilled artisan and involve, for example, homologous recombination between the viral DNA sequences flanking the DNA sequence in a donor plasmid and homologous sequences present in the parental virus (Mackett, et al., *Proc. Natl. Acad. Sci. USA* 79:7415-7419 (1982)). For example, recombinant viral vectors such as a pox viral vector can be used in delivering the gene. The vector can be constructed for example by steps known in the art, e.g. analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector to insert the heterologous DNA. See, U.S. Pat. No. 5,445,953, incorporated herein by reference.

Pox viruses useful in practicing the present invention include orthopox, suipox, avipox and capripoxvirus.

Orthopox virus include vaccinia, ectromelia and raccoon pox. The preferred orthopox is vaccinia. More preferred is a sub-clone of vaccinia having decreased virulence relative to a standard vaccine strain of vaccinia.

Avipox viruses include fowlpox, canary pox and pigeon pox. The preferred avipox is fowlpox.

A preferred suipox is swinepox.

For example, the DNA gene sequence to be inserted into the virus can be placed into a donor plasmid, e.g., an *E. coli* plasmid construct. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. With a parental pox viral vector, a pox promoter is used. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the DNA gene sequence to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al., *J. Virology*, 60:920 (1986) (shope fibroma virus); capripoxvirus: Gershon, et al., *J. Gen. Virol.*, 70:525 (1989) (Kenya sheep-1); orthopoxvirus: Weir, et al., *J. Virol.*, 46:530 (1983) (vaccinia); Esposito, et al., *Virology*, 135:561 (1984) (monkeypox and variola virus); Hruby, et al., *PNAS*, 80:3411 (1983) (vaccinia); Kilpatrick, et al., *Virology*, 143:399 (1985) (Yaba monkey tumor virus); avipoxvirus: Binns, et al., *J. Gen. Virol.* 69:1275 (1988) (fowlpox); Boyle, et al., *Virology*, 156:355 (1987) (fowlpox); Schnitzlein, et al., *J. Virological Methods*, 20:341 (1988) (fowlpox, quailpox); entomopox (Lytvyn, et al., *J. Gen. Virol.* 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al., *AIDS Research and Human Retroviruses* 7:991-998 (1991)] the EcoRI-HindIII fragment, BamHI fragment, EcoRV-HindIII fragment, BamHI fragment and the HindIII fragment set forth in EPO Application No. 0 308 220 A1. [Calvert, et al., *J. of Virol.* 67:3069-3076 (1993); Taylor, et al., *Vaccine* 6:497-503 (1988); Spehner, et al., (1990) and Boursnell, et al., *J. of Gen. Virol.* 71:621-628 (1990)].

In swinepox preferred insertion sites include the thymidine kinase gene region.

In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Vaccines

Live recombinant viruses expressing an immunogenic cell encoded tumor associated antigen can be used to induce an immune response against tumor cells which express the protein. These recombinant viruses may be administered by intradermal scarification, as was conventionally done for small pox vaccination, or by other routes appropriate to the recombinant virus used. These may include among others, intramuscular, subcutaneous, and intravenous routes. Vaccination of a host organism with live recombinant vaccinia virus is followed by replication of the virus within the host.

For parenteral administration, the recombinant vectors will typically be injected in a sterile aqueous or non-aqueous solution, suspension or emulsion in association with a pharmaceutically-acceptable carrier such as physiological saline.

A specific immune response to a tumor associated antigen can be generated by administering between about $10^5$-$10^9$ pfu of the recombinant pox virus, constructed as discussed above to a host, more preferably one uses $\geq 10^7$ pfu. The preferred host is a human. At least one interval thereafter, which is preferably one to three months later, the immune response is boosted by administering additional antigen to the host. More preferably there is at least a second "boost" preferably at least one to three months after the first boost, more preferably 6-12 months after the first boost. The antigen for boosting may be administered using the same pox virus vector. The boosting antigen may be administered as a whole protein, an immunogenic peptide fraction of the protein, or DNA encoding the protein or peptide. The boosting antigen may preferably be administered using a second pox virus vector from a different pox genus, or may be administered directly, for example, purified protein plus an adjuvant or in a liposome formation. Cytokines, e.g., IL-2, IL-6, IL-12, IL-15, or co-stimulatory molecules, e.g., B7.1, B7.2, may be used as biologic adjuvants. The cytokines can be administered systemically to the host, either cytokines or costimulatory molecules can be co-administered via insertion of the genes encoding the molecules into the recombinant pox vector or a second recombinant poxvirus which is admixed with the recombinant poxvirus expressing the TAA.

Adjuvants include, for example, RIBI Detox (Ribi Immunochemical), QS21 (Cambridge Biotech), incomplete Freund's adjuvant or many others.

Generation of Cytotoxic T-Cells

Cytotoxic T-cells specific for a tumor specific antigen can be established from peripheral blood mononuclear cells (PBMC) obtained from a host immunized as discussed above. For example, PBMC can be separated by using Lymphocyte Separation Medium gradient (Organon Teknika, Durham, N.C., USA) as previously described [Boyum, et al., *Scand J. Clin Lab Invest* 21:77-80 (1968)]. Washed PBMC are resuspended in a complete medium, for example, RPMI 1640 (GIBCO) supplemented with 10% pool human AB serum (Pel-Freeze Clinical System, Brown Dear, Wis., USA), 2 mM glutamine, 100 U/ml penicillin and 100 µg/ml of streptomycin (GIBCO). PBMC at a concentration of about $2 \times 10^5$ cells in complete medium in a volume of, for example, 100 µl are added into each well of a 96-well flat-bottom assay plate (Costar, Cambridge, Mass., USA). The antigen or peptides are added into the cultures in a final concentration of about 50 µg/ml and incubated at 37° C. in a humidified atmosphere containing 5% $CO_2$ for 5 days. After removal of peptide containing media, the cultures are provided with fresh human IL-2 (10U/ml) after 5 days and replenished with IL-2 containing medium every 3 days. Primary cultures are restimulated with the same peptide (50 µg/ml) on day 16. $5 \times 10^5$ irradiated (4,000 rad) autologous PBMC are added in a volume of about 50 µl complete medium as antigen-presenting cells (APC). About five days later, the cultures are provided with human IL-2 containing medium as described previously. Cells are restimulated for 5 days at intervals of 16 days.

Cell Therapy

The cytotoxic T-cell can be cultured to amplify its number and then injected back into the host by a variety of means. Generally, between $1 \times 10^5$ and $2 \times 10^{11}$ cytotoxic T-cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional antigen or fragments containing T-cell eliciting epitope(s) may be administered to the patient to further expand the T-cell number. The antigen or epitope may be formulated with an adjuvant and/or may be in a liposomal formulation.

The cytotoxic T-cells can also be modified by introduction of a viral vector containing a DNA encoding TNF and reintroduced into a host in an effort to enhance the anti-tumor activity of the cells. Other cytokines can also be used.

REFERENCE EXAMPLE 1

Construction of Vectors

Pox Viruses

A number of pox viruses have been developed as live viral vectors for the expression of heterologous proteins (Cepko et al., *Cell* 37:1053-1062 (1984); Morin et al., *Proc. Natl. Acad. Sci. USA* 84:4626-4630 (1987); Lowe et al., *Proc. Natl. Acad. Sci. USA*, 84:3896-3900 (1987); Panicali & Paoletti, *Proc.*

Natl. Acad. Sci. USA, 79:4927-4931 (1982); Machett et al., Proc. Natl. Acad. Sci. USA, 79:7415-7419 (1982)). Representative fowlpox and swinepox virus are available through the ATCC under accession numbers VR-229 and VR-363, respectively. The Wyeth strain of vaccinia is available through the ATCC under accession number VR-325.

The parental fowlpox virus is a plaque purified isolate of the POXVAC-TC vaccine strain of fowlpox virus (Schering Corp.).

The parental vaccinia virus (clone B-3-1) is a plaque-purified isolate of the Wyeth strain that was received from Flow Laboratories.

To obtain clone B-3-1, the Wyeth strain of vaccinia was passaged in the fetal rhesus lung line FRhL (ATCC Accession No. CL160) as follows:

| | |
|---|---|
| Pass 1: | Plaque "B" was picked at $10^{-5.3}$ dilution |
| Pass 2: | Plaque "B-3" was picked at $10^{-1.6}$ dilution |
| Pass 3: | Plaque "B-3-1" was picked at $10^{-1.6}$ dilution |
| Pass 4-14 7: | Plaque B-3-1 was serially passaged using serum-free medium with sucrose phosphate glutamate (SPG) to prepare a small seed pool at the 7th passage level. |

The virulence of this plaque isolate of the Wyeth vaccinia strain was assessed by determining the infections dose of the virus lethal to 50% ($LD_{50}$) of weaning mice infected intracranially. Two to three week old immunocompetent mice were inoculated with various doses of virus (7 mice/dose); the $LD_{50}$ was determined on mice succubing between 2 and 12 days post-inoculation by calculating the 50% endpoint using the Reed-Muench method (20). These values were compared to those obtained using a virus stock prepared by expanding virus directly from a vial of the CDC Smallpox Vaccine (Table 1).

TABLE 1

Neurovirulence of Wyeth Vaccinia Virus in Mice

| | $LD_{50}$ (plaque forming units) | |
|---|---|---|
| Experiment # | Wyeth master virus stock | Small pox vaccine |
| 1 | ND* | $10^{5.4}$ |
| 2 | ND | $10^{5.6}$ |
| 3 | $10^{6.7}$ | $>10^6$ |
| 4 | $10^{6.8}$ | $10^{5.4}$ |
| 5 | $10^{7.3}$ | ND* |
| 6 | $10^{7.7}$ | ND |
| 7 | $10^{7.3}$ | $10^{5.7}$ |

*not determined

DNA Vectors for In Vivo Recombination with a Parent Virus

Genes that code for desired carcinoma associated antigens are inserted into the genome of a pox virus in such a manner as to allow them to be expressed by that virus along with the expression of the normal complement of parent virus proteins. This can be accomplished by first constructing a DNA donor vector for in vivo recombination with a pox virus.

In general, the DNA donor vector contains the following elements:
  (i) a prokaryotic origin of replication, so that the vector may be amplified in a prokaryotic host;
  (ii) a gene encoding a marker which allows selection of prokaryotic host cells that contain the vector (e.g., a gene encoding antibiotic resistance);
  (iii) at least one gene encoding a desired protein located adjacent to a transcriptional promoter capable of directing the expression of the gene; and
  (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-, di-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., *J. Virol.*, 62:1046 (1988); Falkner and Moss., *J. Virol.*, 62:1849 (1988); Franke et al., *Mol. Cell. Biol.*, 5:1918 (1985), as well as genes such as the *E. coli* lacZ gene, that permit identification of recombinant viral plaques by colorimetric assay (Panicali et al., *Gene*, 47:193-199 (1986)).

Integration of Foreign DNA Sequences into the Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo dermal (CED) cells, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112, WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK⁻ and can be selected on this basis (Mackett et al., *Proc. Natl. Acad. Sci. USA*, 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing β-galactosidase can be selected using a chromogenic substrate for the enzyme (Panicali et al., *Gene*, 47:193 (1986)).

Following in vivo recombination, recombinant viral progeny can be identified by one of several techniques. The presence of integrated foreign DNA can be detected by hybridization with a labeled DNA probe specific for the inserted DNA. Preferred techniques for selection, however, are based upon co-integration of a gene encoding a marker or indicator gene along with the gene of interest, as described above. A preferred indicator gene is the *E. coli* lacZ gene which encodes the enzyme β-galactosidase. Selection of recombinant virus expressing β-galactosidase can be done by employing a chromogenic substrate for the enzyme. For example, recombinant viruses are detected as blue plaques in the presence of the substrate 5-bromo-4-chloro-3-indolyl-,β-D-galactoside or other halogenated-indolyl-,β-D-galactoside (e.g., BluoGal™).

Characterizing the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA).

EXAMPLE I

Construction of Recombinant Vaccinia Virus (PROSTVAC)

Figure 1:
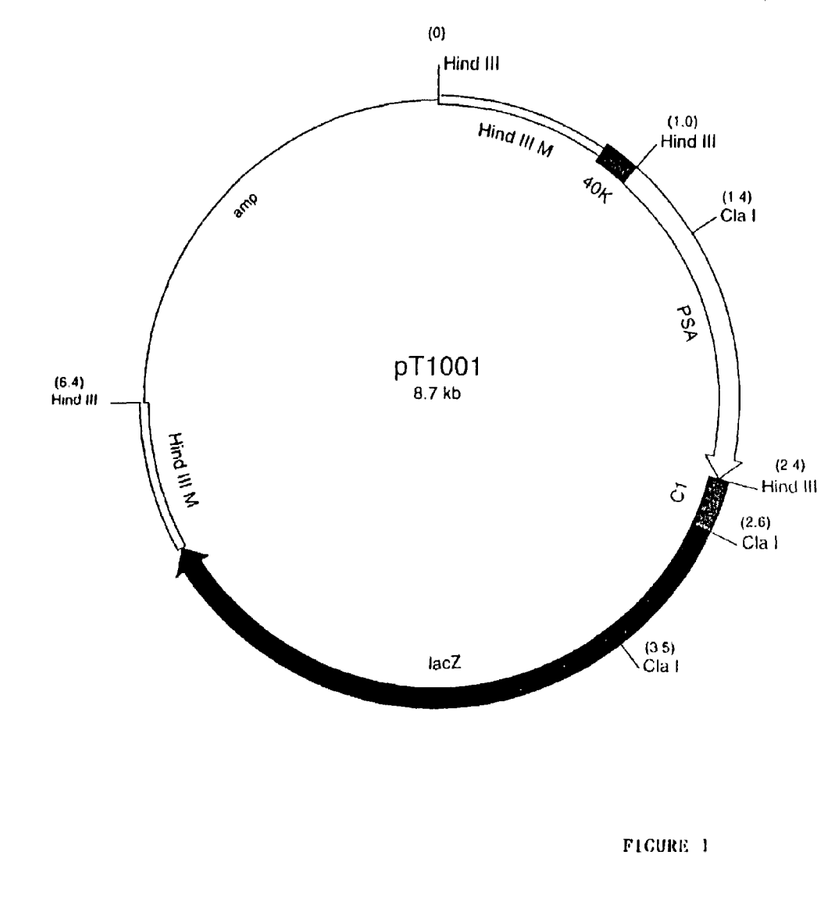
FIG. 1 is a plasmid map of pT1001, the donor plasmid used in the construction of PROSTVAC.
Figure 2:
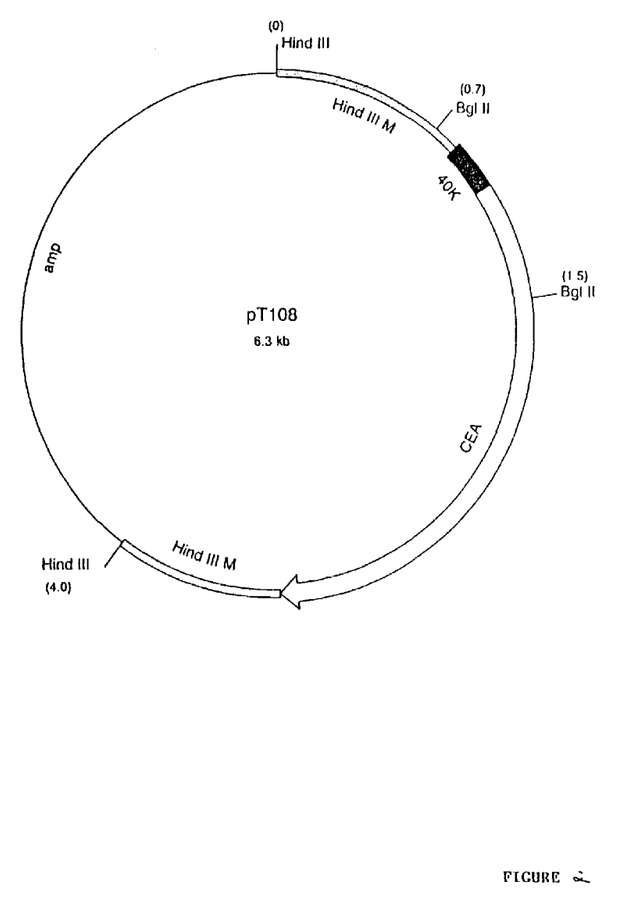
FIG. 2 is a plasmid map of pT108, the donor plasmid used in the construction of TBC-CEA.

A 786 bp DNA fragment encoding the entire open reading frame of human prostate specific antigen was amplified by reverse transcriptase PCR (GeneAmp RNA PCR Kit, Perkin Elmer, Norwalk, Conn.) from total RNA extracted from the human metastatic prostate adenocarcinoma cell line, LNCaP.FGC (CRL 1740, American Type Culture Collection (ATCC), Rockville, Md.). The predicted amino acid sequence derived from the PSA coding sequence was shown to be nearly identical to the published sequence (Lundwall, et al., *FEBS Letters*, 214:317-322, (1987), differing only in a change from asparagine to tyrosine at position 220. The PSA DNA fragment, containing the entire coding sequence for PSA, 41 nucleotides of the 5' untranslated region, and 520 nucleotides of the 3' untranslated region, was inserted into the Xba I restriction endonuclease cleavage site of the vaccinia virus transfer vector pT116. The resulting plasmid, designated pT1001, contains the PSA gene under the control of the vaccinia virus 40K promoter (Gritz, et al., *J. Virol.* 64:5948-5957, (1990), and the *E. coli* lacZ gene under the control of the fowlpox virus C1 promoter (Jenkins, et al., *AIDS Research and Human Retroviruses* 7:991-998, (1991). The foreign genes are flanked by DNA sequences from the Hind III M region of the vaccinia genome. FIG. 1 is a plasmid map of PT1001.

A plaque-purified isolate from the Wyeth (New York City Board of Health) strain of vaccinia was used as the parental virus in the construction of the recombinant vaccinia virus, PROSTVAC. The generation of recombinant vaccinia virus was accomplished via homologous recombination between vaccinia sequences in the Wyeth vaccinia genome and the corresponding sequences in pT1001 in vaccinia-infected $RK_{13}$ cells (CCL 37, ATCC) transfected with pT1001. Recombinant virus was identified using a chromogenic assay, performed on viral plaques in situ, that detects expression of the lacZ gene product in the presence of halogenated indolyl-beta-D-galactoside (Bluo-gal), as described previously (Panacali, et al., 1986). Appropriate blue recombinant viruses were purified by four rounds of plaque-purification. Virus stocks were prepared by clarifying infected $RK_{13}$ cell lysates followed by centrifugation through a 36% sucrose cushion.

EXAMPLE II

Construction of Recombinant Fowlpox Virus (rF-CEA)

The generation of recombinant fowlpox viruses is accomplished via homologous recombination in vivo between fowlpox DNA and a plasmid vector that carries the heterologous sequences to be inserted. The plasmid vectors contain one or more chimeric genes, each comprising a poxvirus promoter linked to a protein coding sequence, flanked by viral sequences from a non-essential region of the fowlpox virus genome. The plasmid is transfected into cells infected with the parental fowlpox virus, and recombination between fowlpox sequences on the plasmid and the corresponding DNA in the viral genome results in the insertion into the viral genome of the chimeric genes on the plasmid.

Figure 3:
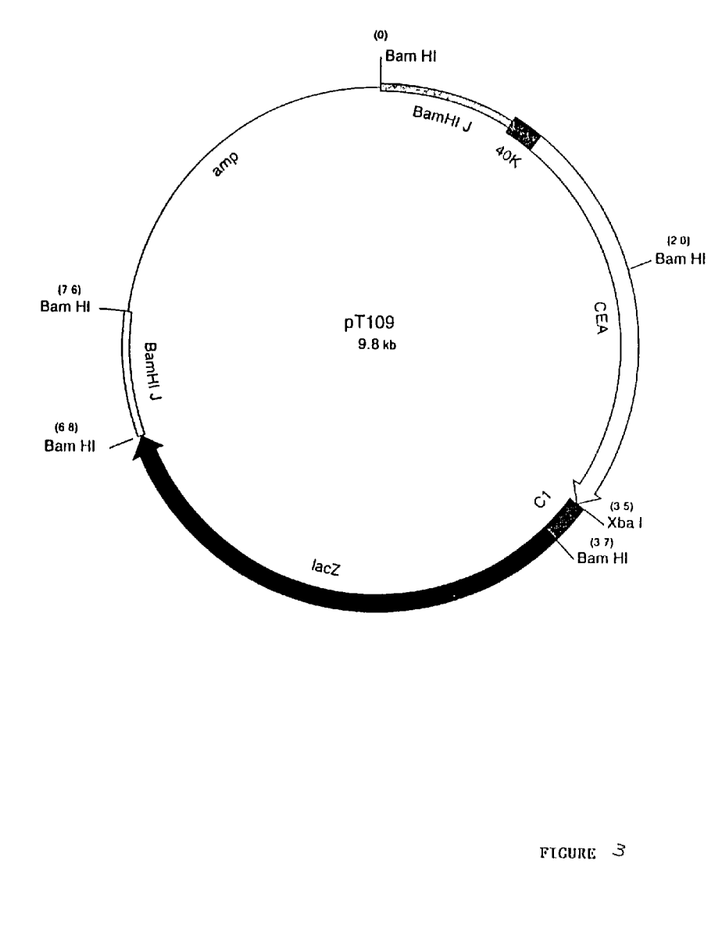
FIG. 3 is a plasmid map of pT109, the donor plasmid used in the construction of rF-CEA.
Figure 4:
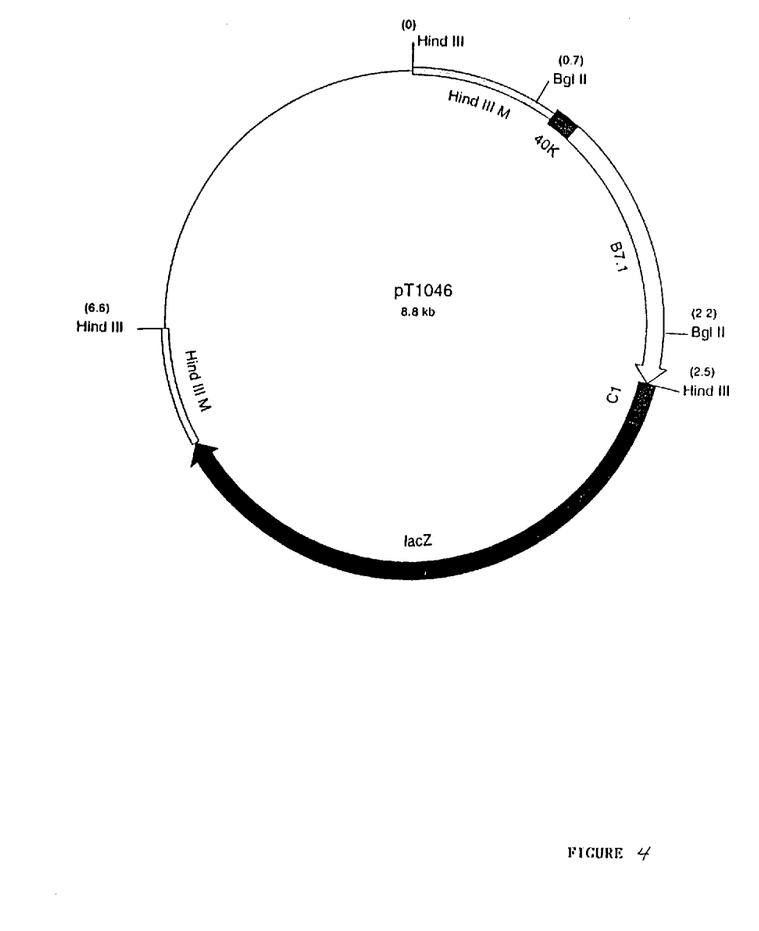
FIG. 4 is a plasmid map of pT1046, the donor plasmid used in the construction of rV-B7.1.
Figure 5:
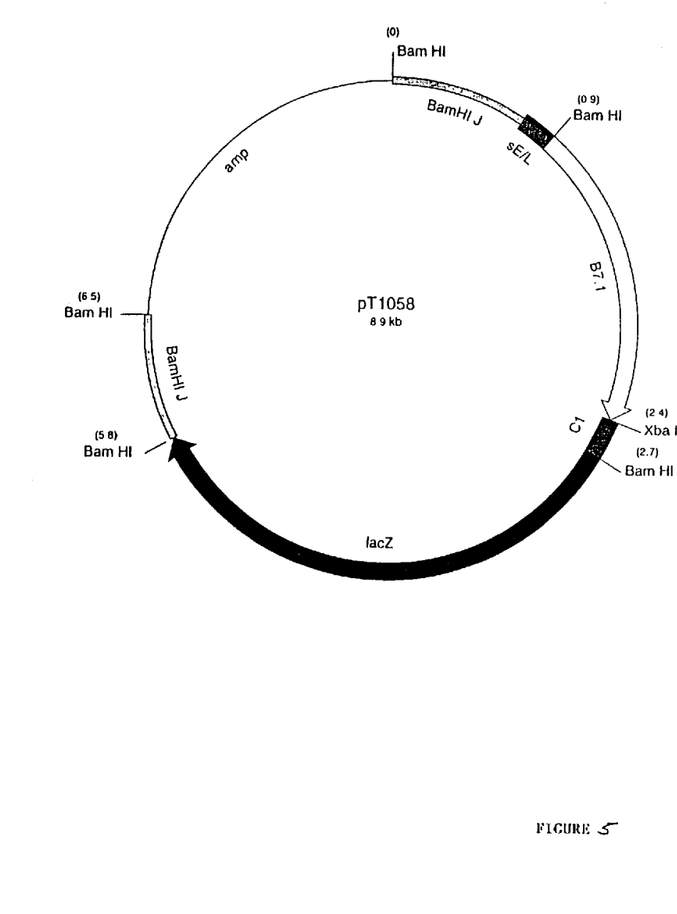
FIG. 5 is a plasmid map of pT1058, the donor plasmid used in the construction of rF-B7.1.
Figure 6:
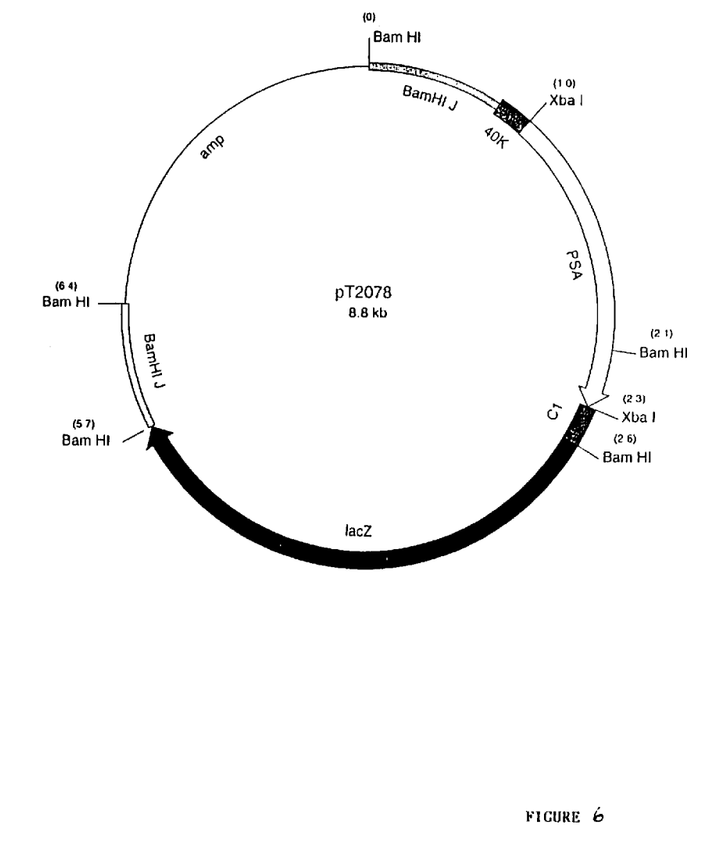
FIG. 6 is a plasmid map of pT2078, the donor plasmid used in the construction of rF-PSA.
Figure 7:
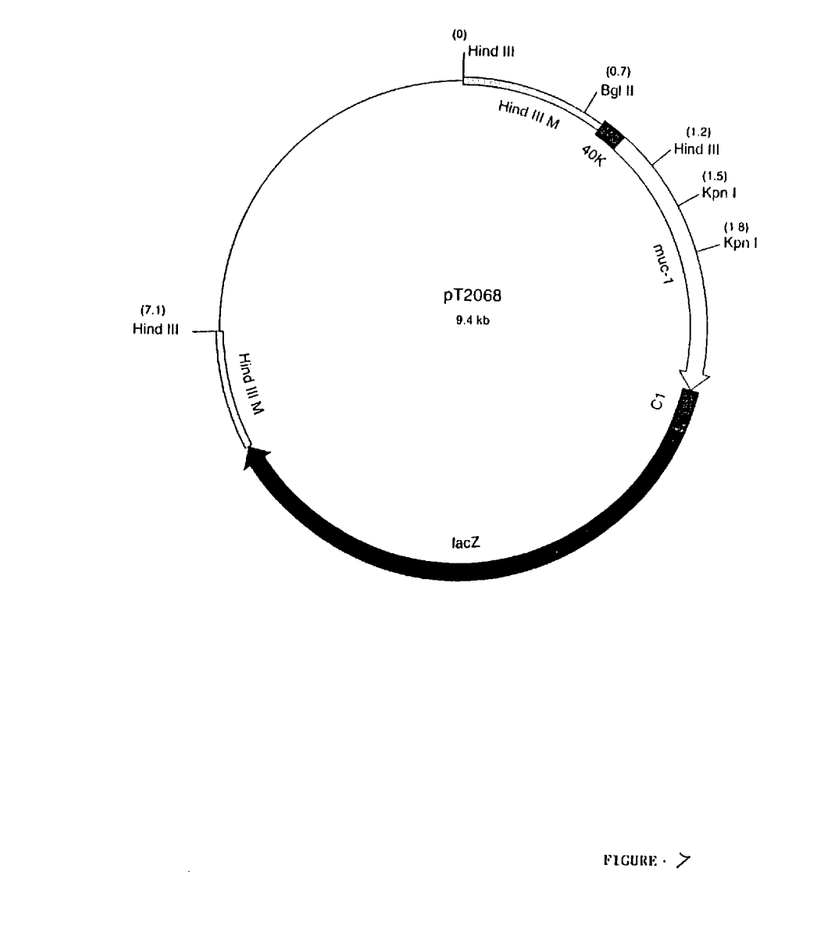
FIG. 7 is a plasmid map of pT2068, the donor plasmid used in the construction of rV-muc-1.

The plasmid vector (pT109) used for insertion of the CEA gene into the parental fowlpox virus genome by in vivo recombination is illustrated in FIG. 3. This vector contains the following elements: (1) a prokaryotic origin of replication to allow amplification of the vector in a bacterial host; (2) the gene encoding resistance to the antibiotic ampicillin, to permit selection of prokaryotic host cells that contain the plasmid; (3) DNA sequences homologous to the BamHIJ region of the fowlpox genome, which direct insertion of foreign sequences into this region via homologous recombination; (4) a chimeric gene comprising the vaccinia 40K transcriptional promotor linked to the CEA gene; (5) a second chimeric gene comprising the fowlpox C1 transcriptional promoter linked to the *E. coli* lacZ gene.

The gene encoding CEA was isolated at the National Cancer Institute from a cDNA library derived from RNA from a human colon carcinoma cell line as disclosed by Kaufman et al., (1991) *Int. J. Cancer* 48, 900-907, the disclosure of which is herein incorporated by reference.

A plaque-purified isolate from the POXVAC-TC vaccine strain of fowlpox virus was used as the parental virus for this recombinant vaccine. In vivo recombination between the plasmid vector and the viral DNA resulted in the formation of a recombinant virus in which the CEA gene, under the transcriptional direction of the vaccinia 40K promoter, and the lacZ gene, under the control of the C1 promoter, were inserted into the BamHIJ region of the fowlpox virus genome.

A chromogenic assay for β-galactosidase was used to identify recombinant viruses containing the lacZ and CEA sequences. This method takes advantage of the ability of fowlpox virus to form distinct plaques when grown on monolayers of CED cells. After in vivo recombination, cells were infected with progeny virus until distinct plaques were visible, at which time the plaques were overlaid with a chromogenic substrate for Beta-galactosidase (Bluo-gal). Viral plaques expressing lacZ appeared blue against a clear background. Positive plaques were picked from the cell monolayer and their progeny were further propagated. Repeated rounds of plaque isolation and replating in a presence of Bluo-gal resulted in the purification of the desired recombinant. Positive recombinants were amplified to produce a seed stock on CED cells. The seed stock was then subjected to titration, genomic and protein expression analysis.

The structure of the plasmid transfer vector was verified by restriction endonuclease digestion using Xba I and BamHI. In addition, the products of digestion with these enzymes were subjected to Southern blot analysis using labeled probes corresponding to the CEA gene and to the fowlpox BamHI J sequences. The DNA fragments visualized by these methods were of the predicted sizes, and the presence of the CEA gene was unequivocally demonstrated, thus confirming the predicted structure of the plasmid.

The recombinant pox virus set forth below in Table 2 can be constructed using similar techniques.

TABLE 2

| RECOMBINANT POX* | DONOR PLASMID | TUMOR ASSOCIATED GENE/IMMUNO-MODULATOR | REFERENCE FOR GENE |
|---|---|---|---|
| TBC-CEA | pT108 | CEA | Beauchemin et al., Mol. Cell. Biol 7: 3221–3230 |
| rF-CEA | pT109 | | |
| rV-B7.1 | pT1046 | B7.1 | Freeman et al, 1989, J. Immunol. 143: 2714–2722 |
| rF-B7.1 | pT1058 | | |
| rF-PSA | pT2078 | PSA | Hodge et al., 1995, int. J. Cancer, 63: 231–237 |
| rV-muc-1 | pT2068 | muc-1 | Gendler et at., 1990, J. Biol. Chem., 265: 15286–15293 |

*rV indicates vaccinia recombinant
rF indicates fowlpox recombinant

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a mammalian host having a tumor expressing a tumor associated antigen (TAA) by enhancing an immune response to the TAA, comprising administering to the host a first pox virus vector system encoding a tumor associated antigen (TAA) in conjunction with a gene encoding B7.1, wherein both the TAA and the B7.1 genes are expressed, and at least one to three months thereafter administering a second pox virus vector system encoding the same TAA as the first pox virus vector system, in conjunction with a gene encoding B7.1, wherein both the TAA and the B7.1 genes are expressed, wherein the second pox virus vector system is from a different pox virus genus than the first pox virus vector system and the tumor associated antigen is carcinoembryonic antigen (CEA).

2. A method of treating a mammalian host having a tumor expressing a tumor associated antigen (TAA) by enhancing an immune response to the TAA, comprising administering to the host a first pox virus vector system encoding a tumor associated antigen (TAA) in conjunction with a gene encoding B7.1, wherein both the TAA and the B7.1 genes are expressed, and at least one to three months thereafter administering a second pox virus vector system encoding the same TAA as the first pox virus vector system, in conjunction with a gene encoding B7.1, wherein both the TAA and the B7.1 genes are expressed, wherein the first pox virus vector system is from an orthopox virus and the second pox virus vector system is from an avipox virus and the tumor associated antigen carcinoembryonic antigen (CEA).

3. The method of treatment of claim 1, wherein the first pox virus vector system is from an avipox virus and the second pox virus vector system is from an orthopox virus.

4. The method of claim 2 or 3, wherein the orthopox is vaccinia and the avipox is fowlpox.

5. The method of claim 1 or 2, wherein the first pox vector system comprises one pox vector containing DNA encoding both B7.1 and the TAA.

6. The method of claim 1, wherein the first pox vector system comprises two pox virus vectors, one vector encoding B7.1 and a second vector encoding the TAA.

7. The method of claim 1 or 2, wherein the second pox vector system comprises one pox vector containing DNA encoding both B7.1 and the TAA.

8. The method of claim 1, wherein the second pox vector system comprises two pox vectors, one vector encoding B7.1 and a second vector encoding the TAA.

9. The method of claim 1 or 2, wherein the mammalian host is a human.

* * * * *